(12) United States Patent
Johnson

(10) Patent No.: US 6,350,243 B1
(45) Date of Patent: Feb. 26, 2002

(54) PORTABLE HEARING THRESHOLD TESTER

(75) Inventor: Daniel L. Johnson, Provo, UT (US)

(73) Assignee: Bruel-Bertrand & Johnson Acoustics, Inc., Montreal (CA)

( * ) Notice: Subject to any disclaimer, the term of this patent is extended or adjusted under 35 U.S.C. 154(b) by 0 days.

(21) Appl. No.: 09/474,197

(22) Filed: Dec. 29, 1999

(51) Int. Cl.[7] ................................................. A61B 5/00
(52) U.S. Cl. ........................................................ 600/559
(58) Field of Search ...................... 600/559, 25; 73/585

(56) References Cited

U.S. PATENT DOCUMENTS

| | | | |
|---|---|---|---|
| 3,809,811 A | * 5/1974 | Delisle et al. | 73/585 |
| 4,024,499 A | * 5/1977 | Bosscher | 600/559 |
| 5,197,332 A | * 3/1993 | Shennib | 600/559 |
| 5,595,178 A | 1/1997 | Voss et al. | 128/653.1 |
| 5,645,074 A | * 7/1997 | Shennib et al. | 600/559 |
| 5,692,509 A | 12/1997 | Voss et al. | 128/653.1 |
| 5,792,072 A | 8/1998 | Keefe | 600/559 |
| 5,795,287 A | 8/1998 | Ball et al. | 600/25 |
| 5,897,494 A | 4/1999 | Flock et al. | 600/407 |
| 5,970,795 A | * 10/1999 | Seidmann et al. | 73/585 |

OTHER PUBLICATIONS

"The Preferred Choice in Audiometric Testing" by Eartone, Division of Cabot Corporation.

* cited by examiner

Primary Examiner—Robert L. Nasser
Assistant Examiner—Brian Szmal
(74) Attorney, Agent, or Firm—Thorpe North & Western, LLP

(57) ABSTRACT

A portable hearing tester to test the temporary hearing threshold shift of an individual. The portable hearing tester has a bone vibrator coupled to a discrete tone generator which is applied to a person's external skull. The bone vibrator is preferably gripped in the teeth. An alternative embodiment of the present invention uses a bone vibrator on the mastoid or forehead. The discrete tones generated through the bone vibrator can be heard by the person to test their current hearing threshold. Between 2 to 12 tones will be played for the person to hear. If the person cannot hear the selected tones at a specific decibel level which could be heard before, then that indicates a hearing threshold shift. Alternatively, discrete levels at one tone can be presented. The person need only count the number of distinct levels heard when the number of tones is reduced. When that number decreases it indicates a hearing threshold shift. The portable hearing tester can also include a two channel dosimeter which provides a way to eliminate a person's voice from the noise measurement.

11 Claims, 5 Drawing Sheets

PORTABLE HEARING THRESHOLD TESTER

TECHNICAL FIELD

This invention relates generally to the field of hearing testing devices, and more particularly to a portable hearing threshold tester which generates a number of test tones.

BACKGROUND ART

Education and training have always been important parts of hearing loss prevention programs. This includes training regarding noise exposure and hearing protection. Unfortunately, it is difficult to convince every person or worker exposed to noise that hearing protection is in their own long range interest. Even when hearing protection is worn, it is a difficult task for hearing conservation professionals to estimate hearing protector performance. There are standardized procedures for rating hearing protectors, but these ratings are for groups of people, not for individuals. An individual may find that a particular hearing protector provides much less or perhaps more protection for them than the average person. In addition, a person may be more sensitive to noise exposure than the average population. For instance, one individual may develop no temporary hearing loss when exposed to 85 dB of noise, where another person may develop 30 dB of temporary hearing loss.

There are procedures for measuring the effectiveness of head set or ear muff type protectors by making measurements under the ear muff. For example, Sound Technologies has introduced a system called the Verifier, for making measurements under an insert type of plug. These testing systems work well to show that an individual can or cannot obtain sufficient protection from a particular type of hearing protector, but they cannot serve as an easy check to see if the protector is fitted properly every time it is actually used. Currently, it is difficult to quickly and efficiently test the effectiveness of hearing protectors.

One standard approach used to check the effectiveness of hearing protectors is to test for any elevation of a person's hearing threshold during or after noise exposure. An audiogram is normally administered by a trained professional use specialized audiometric equipment to test a person's hearing threshold. These current hearing testing devices are large and cumbersome. As a result, they require space for the testing equipment and a quiet area to perform the hearing test. Current hearing testing devices also require the constant attention of a trained professional to test the hearing of the subject. Because a hearing professional is needed to run the equipment, it is unlikely that a hearing test will normally take place on-site where the noise exposure takes place.

Employers, managers, and owners of areas that have a high level of noise exposure are also reluctant to administer frequent hearing tests because of the inherent cost and potential liability. Another problem is that the hearing testing may interfere with an employee's work schedule, if it is performed on a regular basis. Further, employees may consider hearing testing a nuisance and employers are opposed to any decline in productivity it creates. All the factors described above make it difficult to perform on-site hearing testing where high levels of sound exposure exist.

When hearing testing takes place, a person is normally tested to determine their current hearing threshold. A person's hearing threshold is the softest or weakest sound that can be heard. Typically, changes in hearing thresholds come from noise exposure. They may also occur from sickness, head injuries, or exposure to toxic substances such as lead or carbon monoxide. These changes can be either temporary or permanent. With noise exposure, the changes are more likely to be temporary, lasting from a few minutes to many hours or days. This type of temporary hearing loss is known as temporary threshold shift (TTS). In other words, certain tones, i.e., frequencies, at specific sound levels or decibels may temporarily be inaudible to a person who is experiencing TTS. It is important to know if a certain type of noise a person is exposed to is producing TTS. This way the exposure can either be avoided or reduced by using hearing protectors. In the case where hearing protectors are being worn, TTS indicates that the hearing protection is not performing adequately. Being able to quickly and inexpensively test for TTS allows an individual to improve their hearing protection and avoid overexposure to harmful sounds. The current state of the art does not provide any quick, cost-effective or simple method of testing TTS and hearing loss without having a trained professional perform a complete audiogram.

Accordingly, it would be an improvement over the state of the art to provide a new method and apparatus for testing hearing which can be self-administered and does not require a trained professional to administer the test. Another improvement would be to provide a hearing tester which is portable and inexpensive. In addition, it would be advantageous to provide a device which allows an individual to quickly and easily evaluate the performance of a hearing protection device they are using. A further improvement would be to build a hearing tester into a noise measurement device worn by a person such as a noise dosimeter.

OBJECTS AND SUMMARY OF THE INVENTION

It is an object of the present invention to provide a hearing tester for testing a person's hearing without the attention of a skilled professional.

It is a further object of the present invention to provide a hearing tester which is portable.

It is another object of the present invention to provide a hearing tester that is inexpensive and simple to use.

It is another object of the present invention to provide a hearing tester that can be used immediately after noise exposure.

It is yet another object of the invention to provide a hearing tester to enable a person to evaluate the performance of the hearing protection device they are using.

The presently preferred embodiment of the present invention is a portable hearing threshold tester which has a discrete tone generator, which generates a discrete tone with two or more discrete decibel levels near the hearing threshold for each discrete tone. A decibel level which is near the hearing threshold is within approximately 5 decibels or less of the hearing threshold. These tones are passed into a bone vibrator from a speaker coupled to the discrete tone generator. Then the bone vibrator is gripped in the person's teeth who is receiving the test. Accordingly, the discrete tones generated can be heard by the person to test their current hearing threshold.

An alternative embodiment uses a discrete tone sequence or a number of different frequencies which each have separate decibel levels. This embodiment may also use multiple frequencies at each discrete decibel level or multiple decibel levels for certain groups of frequencies. Additionally, the multiple tones or frequencies can be generated at the same decibel level which is just above a person's hearing threshold.

The method for testing a person's hearing threshold uses the steps outlined below. First, a bone vibrator is applied to one or more external bones in a person's head. This bone vibrator is preferably gripped in the teeth. A processor with a memory generates a pre-programmed tone sequence with two or more discrete tones near a hearing threshold with a pre-specified decibel level for each tone. Then, the decibel level is automatically increased and the test is repeated until the person is able to hear at least one of the tones in the tone sequence. Finally, the person who received the test determines which discrete tones have been heard. The number of discrete tones which are not heard, as compared to the number normally heard, determines the threshold of the person's temporary hearing loss.

These and other objects, features, advantages and alternative aspects of the present invention will become apparent to those skilled in the art from a consideration of the following detailed description taken in combination with the accompanying drawings.

DISCLOSURE OF THE INVENTION

Reference will now be made to the drawings in which the various elements of the present invention will be given numerical designations and in which the invention will be discussed so as to enable one skilled in the art to make and use the invention. It is to be understood that the following description is only exemplary of specific embodiments of the present invention, and should not be viewed as narrowing the claims which follow.

This disclosure describes a portable hearing tester device that is small and relatively inexpensive. The device is also compact enough to be carried with an individual so it can be used each time they are exposed to noise. The only testing requirement is that the ambient noise levels should be sufficiently low enough that the noise does not interfere with the hearing test. If a person is wearing hearing protection while performing the test, the ambient noise levels can be higher. Ambient noise is defined as not sufficiently low enough when it is loud enough to mask out one or more of the test tones.

Figure 1:
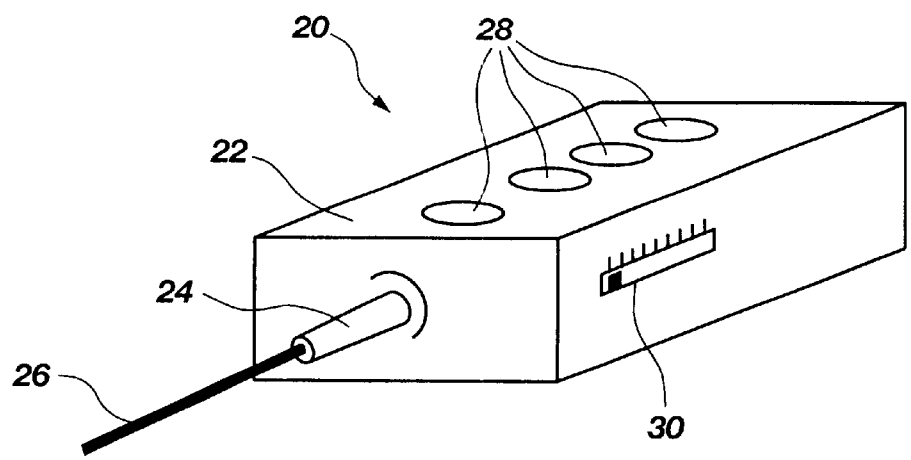
FIG. 1 shows a portable hearing tester with a bone vibrator that is arranged to provide contact with a person's teeth.

Referring now to FIG. 1, a portable hearing tester 20 is shown with a bone vibrator 26 that is configured for contact with a person's teeth. A tone generator 22 is shown which contains the required circuitry to generate test tones or frequencies. The tone generator 22 is shaped and sized so it can be easily held in a person's hand. For example, the tone generator should be several inches in length and from one half inch to two inches in diameter. Convenient shapes such as cylinders or grip shaped housings can be also used to contain the circuitry, if desired. The tones are pre-programmed or pre-recorded into the circuitry contained in the tone generator 22. A speaker (not shown) inside the tone generator produces the actual tones and vibrates the sleeve 24 which holds the bone vibrator 26. The bone vibrator 26 is a toothpick or a short stick, preferably made of plastic, metal or wood. The toothpick transmits the sound vibrations generated by the speaker and transfers the vibrations to the person's teeth. The sleeve 24 or holding device should be strong enough to withstand the insertion and removal of the toothpicks on a regular basis. The vibrations pass from the bone vibrator 26 into the teeth, and produce sounds in the person's ear who is being tested. It should also be realized that the bone vibrator 26 does not necessarily need to be cylindrical or toothpick-shaped, although it is preferred. The bone vibrator 26 could also be flat with a flat sleeve, or contain a square or knobbed end. One could also imagine that it could be triangular or molded into some other decorative shape by injection molding.

A major advantage of using a bone vibrator on the teeth is that a consistently repeatable auditory signal is produced. It is much easier to get good physical contact with the teeth than with other bones in a person's head. Essentially, a person can bite down on the bone vibrator and hold it between their teeth. A bone vibrator which is used on the teeth also allows the test tones to be transferred more efficiently to the ear. A conventional bone vibrator used for auditory testing is used on either the forehead or on the mastoid behind the ear. When a bone vibrator is used on the forehead or mastoid there is a certain amount of skin tissue between the bone and the bone vibrator which can reduce the level of the tones being generated. This reduction can produce incorrect test results. Further, the sounds generated by the bone vibrator may vary slightly depending on where the bone vibrator is situated. The preferred embodiment of the current invention avoids the sound reduction or variation by applying the vibrations directly onto a bone surface such as the teeth. Another result of using a bone vibrator on the teeth is that the tones or frequencies generated are heard clearly in both ears, or the better ear if there is a substantial difference in the auditory threshold between the ears. The changes in the better ear are normally considered more important than the changes in the worse ear. This means that only one bone vibrator can be used to test both the ears simultaneously. In the case where the worse ear needs to be tested, the hearing tester will have an output jack so a conventional headset can optionally be used to test the worse ear.

Using a toothpick as the bone vibration mechanism has yet another benefit. The benefit is that the toothpick can be disposed of very easily. This is a very inexpensive and sanitary method of testing the hearing. There is no need for more expensive earplugs, because very cheap toothpicks can be used. Avoiding the use of a headset also means that the headset does not need to be cleaned or sanitized. It is also very simple for multiple individuals to use the same portable hearing tester without any sanitary concerns because each individual can use their own sanitized toothpick.

There are many other advantages afforded by this invention. It should be immediately apparent that one advantage of this invention is that a small hand sized hearing tester is produced. This is in contrast to a normal audiometric testing station, which is the size of a small suitcase and typically requires a headset of some sort. The large size and cost of an audiometer makes it inconvenient to give an audiogram on site in a construction area, excavation site or similar remote areas. Because of the current invention's size, it is very portable and can be used at any location with ease.

This invention can be used in any common workplace, home setting or recreational setting without professional supervision. First, in a quiet location such as a bedroom at home, during a relatively quiet period of the workday, or in an audiometric booth, a baseline hearing measurement must be made by the person performing the self test. The initial measurement of the person's hearing hearing threshold level serves to set the individual's baseline for the number of discrete tones or levels heard. This should be done before the start of the activity or shift. These activities may include things such as operating loud equipment, blasting, firearm use, driving loud vehicles or similar uses. Then subsequent measurements are made after noise exposure and when the sound level at the tympanic membrane is the same level as it was during the initial measurement. In other words, both the initial test and the subsequent test should have approximately the same amount of ambient sound when the test is taken. Comparing these two measurements guarantees that an accurate hearing threshold shift level can be obtained. The portable hearing tester can also be built into a noise dosimeter. One of the benefits of building the portable hearing tester into a noise dosimeter is that it is possible to assure the ambient noise level is sufficiently low during testing. Another benefit of combining a portable hearing tester with a noise dosimeter is that the noise dosimeter allows for the measurement of potentially hazardous tones. Hazardous tones are those tones to which the person may be specifically subjected in a certain area. For example, a person may be subject to noise from an assembly line with a specific frequency. In this case, a noise dosimeter can detect that the person is receiving harmful noise doses at the specific frequency and then that frequency or frequency band can be specifically tested with the portable hearing device. Although the portable hearing tester is not a substitute for a complete audiogram, it allows for a simple yet effective test to be administered wherever the user desires.

It is important to note that the amount of background noise that exists when the test is being taken is significant. Even a small amount of background noise, such as people talking, vehicle traffic, or a loud ventilation fan can obscure the tones that would normally be heard in the test without background noise. Hearing protection or earplugs can be used to block out some or most of the background noise to ensure that a correct test baseline level is being produced. When the hearing tester is used in an area where there is constant noise, such as an assembly line or a textile mill, the person who desires to perform the hearing self-test will need to wait until the end of their work shift or find a quiet place to perform the test during a break. Where the noise is not constant, such as a jackhammer, chainsaw or lawnmower, it may be very simple to stop the machine and then find a quiet area for the test.

Referring again to FIG. 1, there are several buttons 28 that are incorporated into the tone generator and are connected to the tone generation circuitry. These buttons 28 are normally open contact switches and can be programmed to have a number of possible functions that are important to this invention. One button can be programmed to start a pre-programmed testing sequence. Another button can be used to increase the decibel level of the frequencies and another button can be used to decrease the decibel level. Yet another can be programmed to control whether the tone sequence is a series of increasing tones or decreasing tones. It should also be apparent that other functional buttons could be added based on the functionality combined into a certain testing unit.

In an alternative embodiment, each of the buttons 28 is programmed to generate a specific frequency tone. This embodiment will have a number of buttons corresponding to the number of tones desired in the testing. There would preferably be between two to twelve buttons 28 on the tone generator 20, one for each of the desired tones. Of course any number of buttons and tones a could be used. Also shown in FIG. 1 is a slidable multiple contact switch 30 which is an alternative configuration to allow the decibel level of the generated frequencies to be increased. The person being tested by the device should start at the lowest possible decibel level they can hear and decrease the decibel level until there are tones that they cannot hear.

As mentioned, using hearing protection while the signals are generated through the bone vibrator is the most effective, because hearing protection can be worn to block out ambient background noise. The typical signal pattern would be a sequence of tones from 250 Hz to 8000 Hz about 1 or 2 seconds in duration. One preferred sequence would be 500, 1000, 2000, 3000, and 4000 Hz. An alternative sequence that can be used is 250, 500, 1000, 2000, 3000, 4000, 6000, and 8000 Hz. Using five or six frequencies normally gives a broad enough range of frequencies to create a useful hearing threshold test. Of course, only three or four frequencies can be used to simplify the test if needed. An important alternative to using a different frequency for each tone generation period is to use the same frequency as the decibel level increases.

An alternative embodiment uses a discrete tone sequence or a number of different frequencies with two or more discrete decibel levels. For example, each tone or frequency may be programmed to have its own decibel level. This embodiment may also use multiple frequencies at each discrete decibel level or multiple decibel levels for certain groups of frequencies. The means that a certain group of frequencies may be automatically generated at one decibel level and another preselected group of frequencies may be generated at another decibel level. Additionally, a sequence of multiple tones can be generated at the same decibel level just above a person's hearing threshold.

Figure 2A:
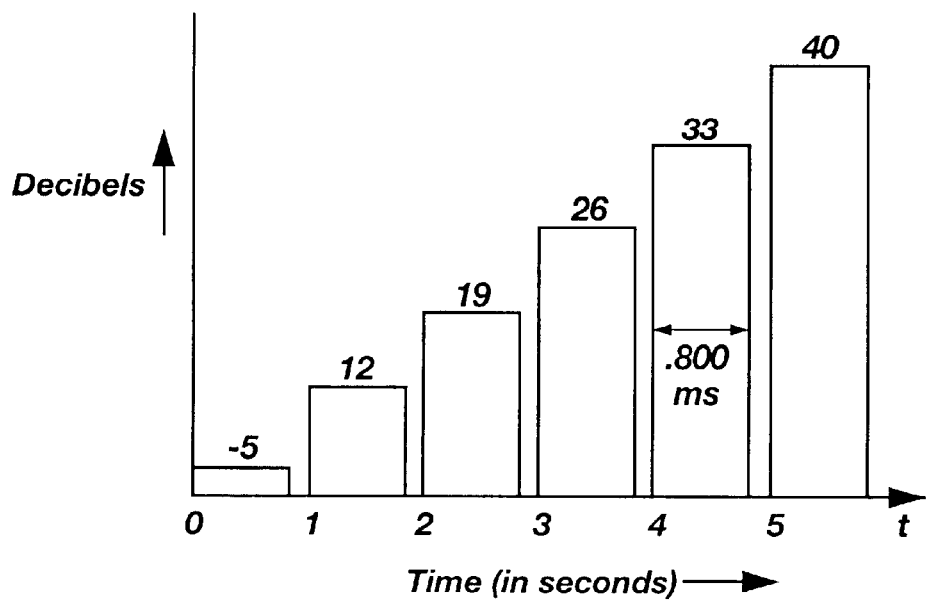
FIG. 2a is a graph of a pre-programmed tone sequence where the sound level of each frequency step is raised by 7 decibels.

FIG. 2a shows a chart of 6 decibel levels generated in sequence. For each pre-recorded or pre-programmed tone the play time is 800 milliseconds and the off-time is 200 milliseconds. After the pause following each tone, the sound level is raised by 7 decibels. Although 7 to 8 decibels is the preferred increase in the sound level, other set increments could be used to increase or decrease the decibel level. As mentioned, the tone which is used at each level may be the same tone for each decibel level or it may be an increasing or decreasing tone sequence as the decibel level increases.

It should also be apparent from this disclosure that other time combinations can be used to play a tone and for silence. For example, the play time for a tone could be 600 milliseconds and the off-time (silence) could be 200 or 400 milliseconds. It is preferable that the total time taken for each on-off sequence is about 1 second. The total duration of the sequence shown in FIG. 2a is approximately 6 seconds or about 1 second for each tone generated. Using a pre-programmed test with tones of pre-set lengths provides a very quick and effective test to determine if TTS or more permanent hearing damage has occurred. Since the test only takes a few seconds, it tests the hearing of a person and saves valuable time and money that might otherwise be consumed by frequent audiograms. It is believed that regular tests will be given with this device in situations where no testing has been done in the past because it was too inconvenient or costly.

As mentioned, the preferred embodiment increases the sound level of each frequency in 7 decibel steps. Each level will be approximately 2.239 times greater than preceding voltage level for the preceding frequency. Then means that the voltage of the last frequency will be 126 times the voltage of the first level. For example, if the voltage starting level needed to be at 1 millivolt then the final level will be 260 millivolts. The starting level should be such that it results in a level at the inner ear that is more that 50% of the lowest normal hearing threshold that 14–20 year-olds can hear. This level will vary with the frequency, with 3000 Hz being the frequency with the lowest starting voltage. If the beginning frequency is 1000 Hz, the voltage for 1000 Hz should be 4.2 times the base voltage at 3000 Hz. The voltage at 2000 Hz is 1.12 times that of 2000 Hz, 4000 Hz is 1.88 times the base voltage, 6000 Hz and 8000 Hz are 3.16 times the base voltage used for 3000 Hz. It is also important that the base voltage level at 3000 Hz be set just above the noise floor for the signal processing chip. The sound processing circuit should contain at least one amplifier and at least one adjustable gain potentiometer to calibrate the voltages of the current invention.

Figure 2B:
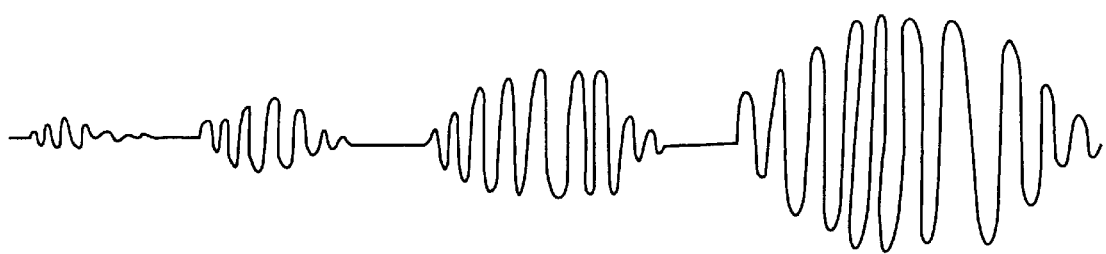
FIG. 2b shows a sine wave of four tones with increasing decibel levels.

FIG. 2b shows that the actual envelope of the waveform should be increased slowly so distortion can be avoided. If the signal goes from zero to the full amplitude level instantaneously, then distortion and popping will be heard by the user. FIG. 2b shows 4 tones played sequentially for one second each, including an intermediate pause.

Figure 3:
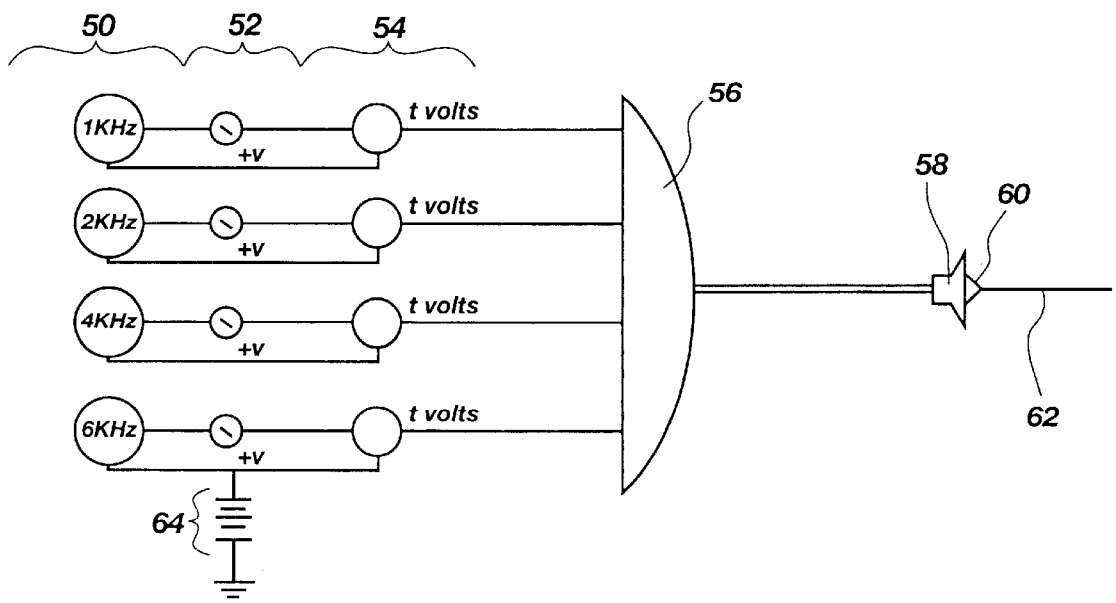
FIG. 3 shows a simplified schematic diagram of the circuitry in a portable hearing tester.

FIG. 3 shows a simplified schematic diaphragm of the circuitry in a portable hearing tester. The tones which will be generated are sampled and stored in one or more memory devices 50. The signal is retrieved from the memories, reproduced by a signal processor (not shown) and passed through one or more variable gain circuits 52. The preferred embodiment of the variable gain circuits is a variable gain potentiometer. A series of normally off contact switches 54 are shown depicting one embodiment of the invention. The switches control the tone being generated at any given time. The generated signal is then amplified through the amplifier 56 and supplied to the speaker 58 or transducer. The speaker 58 is coupled to a sleeve 60 or some equivalent means for holding a toothpick 62 such as a clamp or threaded washer system. When the tones are generated through the speaker it makes the sleeve 60 and toothpick 62 in the sleeve 60 vibrate. It should also be realized that in some embodiments only one contact switch 54 may be used to start a descending or ascending series of tones. The tone sequence would be regulated by the signal processor to control the order and number of tones as pre-programmed into the memory.

The portable hearing tester will normally be in a powered down state. When the button is pushed to start a tone sequence or generate a specific tone, then power is provided until the pre-programmed sequence ends. A power cell 64 or battery is used to power the device. Because the device is portable the most desirable size of batteries is AAA or some other small size.

Figure 4:
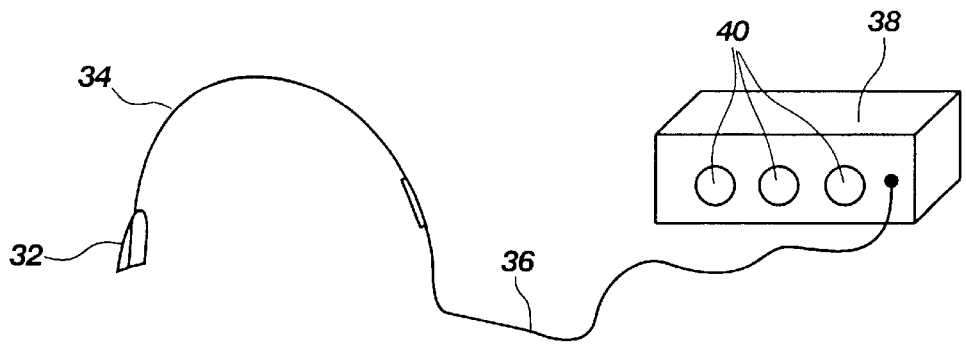
FIG. 4 shows a hearing tester with a headset which can be placed on the mastoid or the forehead.

FIG. 4 is a portable hearing tester with a headset which can be placed on the mastoid or the forehead. The bone vibrator 32 is mounted on a headset 34 which can be place over the person's head who is being tested. The bone vibrator 32 is electrically connected to a tone generator 38 which generates tone sequences as described above. It is important to note that the preferred embodiment of this invention has a bone vibrator to be used on the external bones of the head or skull. The primary areas for application of bone vibrators on the skull as described in this disclosure are places such as the mastoid, forehead, teeth or similar areas. The signal can also be used to drive a speaker in the ear to test one ear at a time, if desired. The buttons 40 shown on the tone generator 38 can be programmed as needed for the specific application. More specifically, one button may be programmed to start a descending sequence of tones. A second button may be configured to increase the decibel level of the tones and a third button would decrease the decibel level of the tones. In an alternative embodiment, a button could be provided on the tone generator 38 for every tone desired to be tested. This might result in anywhere from two to twelve buttons or even more, depending on the tones desired to be tested. The major advantage of a portable hearing testing device as shown in FIG. 4 is that the pre-recorded tone sequence can be played just by pressing a button. This provides a simple, effective test that can be administered in 10 or 15 seconds without the fine tuning and adjusting that must take place in a standard audiogram. In addition, the tone generator 38 can be electronically miniaturized which makes it very portable. For example, because the tone generator can be reduced to a size similar to or smaller than a stereo radio headphone device, then the test can be performed in any location. This is in contrast to the large briefcase-sized machine required for performing audiograms.

Now the method for using this device will be described. As outlined, this device is used after the exposure to noise. The person, who desires to test their own hearing, should find an area where the ambient noise is sufficiently low. A baseline test should have been created prior to the noise exposure and hearing threshold test. Although the test can be performed without hearing protection, it is most effective when the subject is wearing hearing protection. In one embodiment of the invention, the hearing tester contains an indicator light which will indicate when the ambient background sound is low enough to perform the test. The person can begin the self-administered test when the ambient noise is low enough. After pressing a button, the subject listens to the tone sequence through the bone vibrator. The tone sequence is preferably a five or six tone sequence. If one or more of the tones cannot be heard, this indicates that a Temporary Threshold Shift (TTS) of the subject's hearing has occurred. This may mean that the subject's hearing protection is not providing adequate protection at the missing tones at the specified decibel levels. The preferred gain is 10 dB, which shifts all the tones up by 10 dB. If some of the tones are not heard the first time, the gain can be increased. Then the subjects hearing can be retested at the new decibel level. If the subject does not hear some of the tones the second time with the gain increased 10 dB, the person's TTS is probably more than 15 dB at those frequencies. This gives an immediate warning to the person performing the self-test, that the protection being worn is not adequate for that particular noise.

The gain levels of the hearing tester can also be adjusted for a specific individual using that person's baseline audiogram. Alternatively, the hearing tester can be adjusted using two sets of hearing protection (i.e. ear plugs and ear muffs) in a location which has less than 45 dB of ambient noise on average. This allows the gain to be adjusted appropriately for that individual without a baseline audiogram. Each tone frequency may also have a separate gain control (as shown in FIG. 3) so the gain for the specific frequency can be increased in 5 or 10 dB steps. This allows the subject using the tester to detect the magnitude of the temporary threshold shift (TTS) they are experiencing. A check may also be used on a person who has not had exposure to significant noise sources but desires to test any cumulative threshold shift since the last time they used the portable hearing testing device.

In a preferred embodiment of the invention, the starting sound level for the set of increasing decibel levels using one tone is at a fixed level. This is advantageous because only one pre-programmed arrangement needs to be used and can be reused for any number of subjects. The drawback to this method is that the number of levels heard by an individual can be different for each tone. A person with an existing hearing loss at some frequency might hear only two levels, one level or even no tone at all. Because the lowest level that a person hears using a fixed starting level is not necessarily near that person's threshold, errors are built into the TTS (temporary threshold shift) measurement that would not be present if the starting level is set to be just above the person's lowest auditory threshold.

As a result of the disadvantages outlined in the paragraph above, an alternative embodiment the hearing testing instrument can be constructed to allow the gain for each tone tested to be adjusted. The gain should be initially set so that the subject hears all of the discrete tones or frequencies at the lowest possible decibel level. Then the gain should be adjusted downward until the person cannot hear one of the tones. Then the gain should be increased in small steps until the original number of levels is heard. If the test has been taken before sound exposure and then after, the change in the tests will show the amount of hearing threshold shift that has occurred as a result of the sound exposure.

Figure 5:
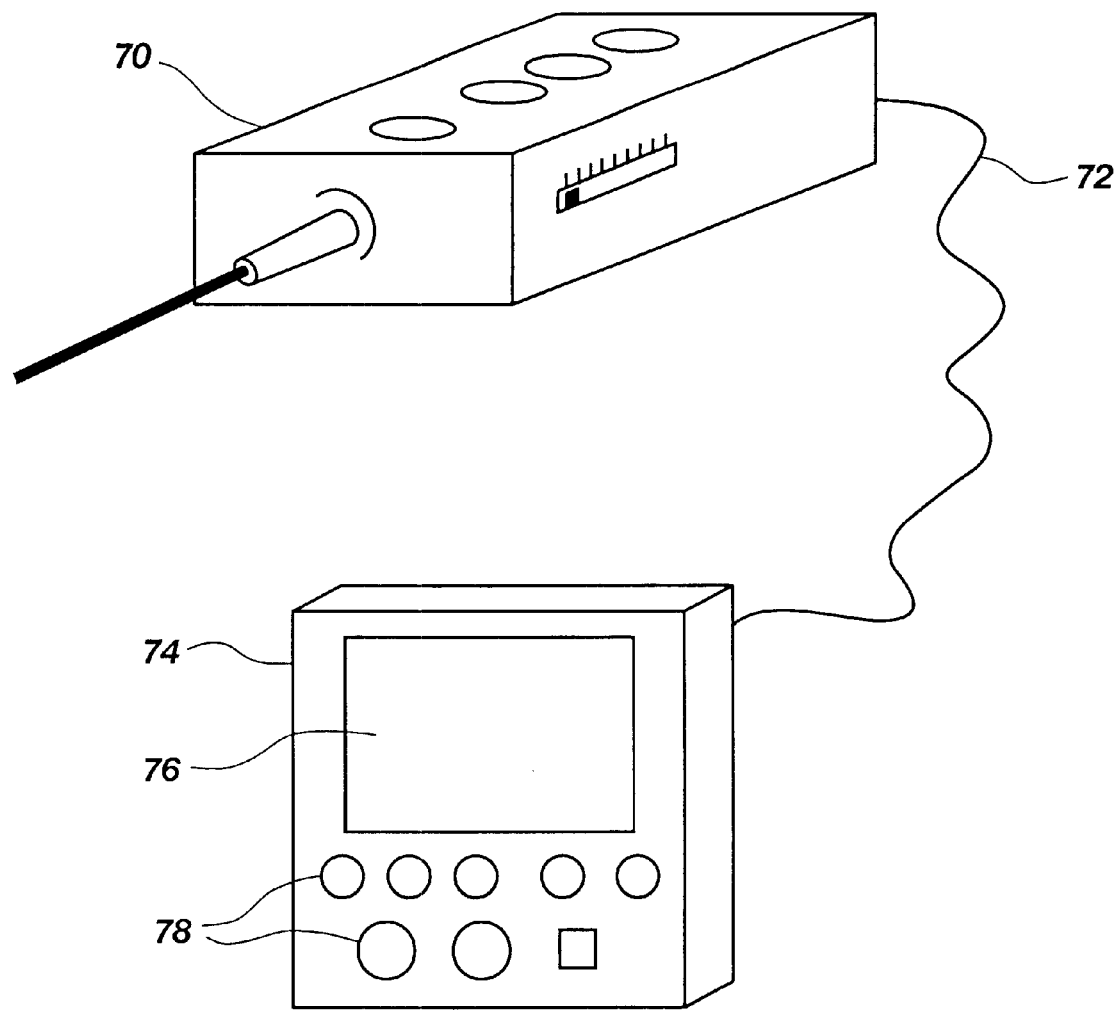
FIG. 5 is a portable hearing tester with a bone vibrator connected to a remote control device.

A drawback of consistently using the same number of discrete levels is that a person who is receiving the test can simply report that they heard all of the levels when they were not actually heard. If the portable testing device is being used by an individual as a self-contained unit which cannot be monitored by a third party, there is no practical way to avoid this type of cheating. The person receiving the self-contained test can report a different result than was actually heard. To overcome this drawback, the portable hearing tester can be configured so that it is attached to a remote monitoring station or to a dosimeter worn by the person. The methods described above are then used to administer tests for TTS. Doing this allows a third party or a microprocessor in the dosimeter to control certain aspects of the test. FIG. 5 shows a portable hearing tester 70 which is electrically coupled to a separate monitoring station 74, which also has a display screen 76 and a plurality of controls 78. The tone sequence produced can be administered with the controls 78 on the monitoring station 74.

The hearing threshold for each tone to be tested would be stored in the computer's memory and this threshold would be used to start the sequence of some number of discrete tones. In addition, some sequences can be programmed to have one or more periods of quiet before the first tone began. Certain controls 78 can also be provided to change the number of tones produced in a sequence. These settings are controlled from the monitoring station or microprocessor in the dosimeter. Then an individual being tested would not be able to tell if they had a temporary threshold shift (TTS) or if the number of discrete levels was changed. A person trying to hide TTS will be caught when using this system because the person will say they heard more discrete levels than was provided. Other methods can be used to avoid cheating on this test when testing for TTS. For example, a sequence of descending tones could be given instead of ascending.

Figure 6:
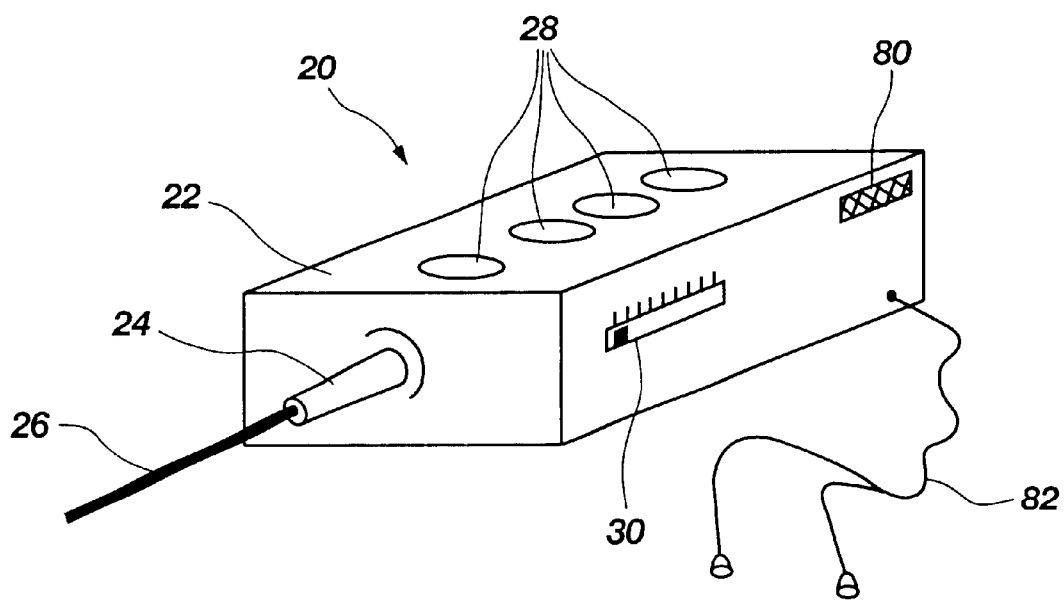
FIG. 6 shows a portable hearing tester with a bone vibrator and microphones.

An important alternative embodiment of the invention uses a noise dosimeter with two microphones. Referring now to FIG. 6, two microphones 82 are shown connected to the portable hearing tester. These two microphones can be positioned in a number of ways. In one configuration, both microphones are on each shoulder of the person being tested. This arrangement provides information regarding which ear is receiving the greatest noise exposure. The resulting information can be used to determine the cases in which testing only one ear is more appropriate.

In another configuration, one of the microphones is used under an insert type of hearing protector worn by the person being tested. The other microphone is placed on the shoulder of the person being tested. The two microphones in this configuration serve several purposes. First, the microphones can detect when the ambient noise level is low enough to begin a tone sequence test. Second, using the combination of the two microphones allows the portable hearing tester to determine whether the person being tested is speaking. If the person is speaking at a given point in time, the sound level measured under the plug may be as great or greater than the sound measured at the shoulder. This effect is due to the occlusion effect and allows the dosimeter to keep track of the noise exposure that is most likely due to the person's vocalization. The microphone underneath the hearing protection also provides the advantage that instantaneous and long term information can be gathered about the hearing protection. For example, if the microphones are under the hearing protection while the person is being exposed to noise, then the amount of noise passing through the hearing protection can be measured. This is valuable because then the quality of the protection provided by the hearing protection can be evaluated. A single microphone 80 mounted on the hearing tester 20 can also be used to measure the ambient noise and control when the test can be given.

It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A portable hearing tester for testing a person's hearing, comprising:
    (a) a discrete tone generator to generate a pre-determined discrete level sequence having two or more discrete decibel levels near a hearing threshold for each discrete tone; and
    (b) a bone vibrator coupled to the discrete tone generator and configured for contact with a person's teeth wherein the discrete levels are transferred through the teeth and can be heard by the person to test a current hearing threshold.

2. The portable hearing tester as in claim 1 wherein the two or more discrete decibel levels in the discrete tone sequence further comprises the same discrete tone for each discrete decibel level.

3. The portable hearing tester as in claim 1 wherein the discrete level sequence further comprises two or more discrete tones selected from the group of discrete tones consisting of 250, 500, 1500, 2000, 3000, 4000, 6000 and 8000 Hertz.

4. The portable hearing tester as in claim 1 wherein the two or more discrete decibel levels in the discrete level sequence use a number of tones from 2 to 8 tones.

5. The portable hearing tester as in claim 1 wherein the two or more discrete decibel levels in the discrete level sequence further comprises a random number of tones between 3 and 12 tones.

6. The hearing tester as in claim 1 further comprising:
    a processor, coupled to the tone generator, to control the random number of tones; and a noise dosimeter coupled to the processor and the tone generator.

7. A portable hearing threshold tester to test a person's hearing, comprising:
(a) a discrete tone generator to generate a discrete tone sequence having two or more discrete tones near a hearing threshold for each discrete tone;
(b) a bone vibrator coupled to the discrete tone generator and adapted to be applied to a person's teeth wherein the discrete tone generated can be heard by the person to test a current hearing threshold; and
(c) a noise level measuring means coupled to the discrete tone generator, for measuring an ambient noise level, wherein the test is initiated when the ambient noise level is sufficiently low.

8. A method for testing a person's hearing threshold, comprising the steps of:
(a) applying a bone vibrator to one or more external bones in a person's head wherein the bone vibrator is coupled to a tone generator;
(b) using two microphones coupled to the tone generator to check noise levels before testing, wherein one microphone is inside a hearing protector and another microphone is outside the hearing protector, to provide information about the hearing protector performance;
(c) generating a tone sequence through the tone generator, having two or more discrete tones near the hearing threshold for each tone; and
(d) determining which discrete tones have been heard, wherein the discrete tones which are not heard determine a threshold of the person's temporary hearing loss.

9. A method for testing a person's hearing threshold, comprising the steps of:
(a) applying a bone vibrator to one or more external bones in a person's head wherein the bone vibrator is coupled to a tone generator;
(b) using two microphones coupled to the tone generator to check noise levels before testing, wherein one microphone is under a hearing protector and another microphone is outside the hearing protector to eliminate a person's voice from a dosimeter's measurements;
(c) generating a tone sequence through the tone generator, having two or more discrete tones near the hearing threshold for each tone; and
(d) determining which discrete tones have been heard, wherein the discrete tones which are not heard determine a threshold of the person's temporary hearing loss.

10. A method for measuring a person's hearing threshold, comprising the steps of:
(a) generating a tone sequence having two or more tones near a hearing threshold for each tone using a discrete tone generator;
(b) using two microphones coupled to the tone generator, wherein one microphone is under a hearing protector and another microphone is outside the hearing protector to detect whether a person being tested is speaking;
(c) eliminating a person's voice from noise measurements made by a noise dosimeter; and
(d) determining which discrete tones have been heard, wherein the discrete tones which are not heard determine a threshold of the person's temporary hearing loss.

11. A method for measuring actual noise exposure for a person, comprising the steps of:
(a) measuring a total noise exposure for the person through a noise dosimeter;
(b) using two microphones coupled to the noise dosimeter, wherein one microphone is under a hearing protector and a second microphone is outside the hearing protector to detect when a person is speaking;
(c) eliminating a person's voice from the total noise exposure measurement made by the noise dosimeter to determine the actual noise exposure for the person.

* * * * *